United States Patent [19]
Kendrick

[11] 4,211,218
[45] Jul. 8, 1980

[54] SPINAL RESTRAINT DEVICE

[76] Inventor: Richard L. Kendrick, 835 Taft St., El Cajon, Calif. 92020

[21] Appl. No.: 933,460

[22] Filed: Aug. 14, 1978

[51] Int. Cl.$^2$ .............................................. A61F 5/04
[52] U.S. Cl. .................................. 128/87 R; 5/82 R; 128/134
[58] Field of Search .............. 128/133, 134, 78, 87 R, 128/87 B; 5/81 R, 82 R, 82 B, 89

[56] References Cited
U.S. PATENT DOCUMENTS

| | | | |
|---|---|---|---|
| 2,309,464 | 1/1943 | Lucci et al. | 5/89 |
| 2,489,828 | 11/1949 | Springer | 5/82 |
| 2,753,864 | 7/1956 | Weidemann | 128/87 R |
| 2,957,475 | 10/1960 | Drake | 128/87 R |
| 3,158,875 | 12/1964 | Fletcher | 5/82 |
| 3,469,268 | 9/1969 | Phillips | 5/89 |
| 3,724,453 | 4/1973 | Dixon et al. | 128/87 R |
| 4,143,654 | 3/1979 | Sherman | 128/134 |

*Primary Examiner*—Lawrence W. Trapp
*Attorney, Agent, or Firm*—Charles C. Logan, II

[57] ABSTRACT

A spinal restraint device in the form of a body member having a head support portion, a neck support portion, and a back support portion. The back support portion and the neck support portion have a body wrap-around arm portion extending laterally from each of its sides. The body member has a front sheet-like layer of flexible material, a middle sheet-like layer of flexible material, and a rear sheet-like layer of flexible material. Laterally spaced longitudinal rows of stitching secure the front, middle, and rear sheet-like layers of flexible material together to form a plurality of longitudinal sleeves between the front sheet-like layer of flexible material and the middle sheet-like layer of flexible material. The longitudinal sleeves extend substantially across the entire width of the body member. Stiffener members are located within the longitudinal sleeves. The spinal restraint device has a pair of leg loop straps attached to the rear surface of the back support portion and a hoisting loop attached to the rear surface of the head support portion.

8 Claims, 3 Drawing Figures

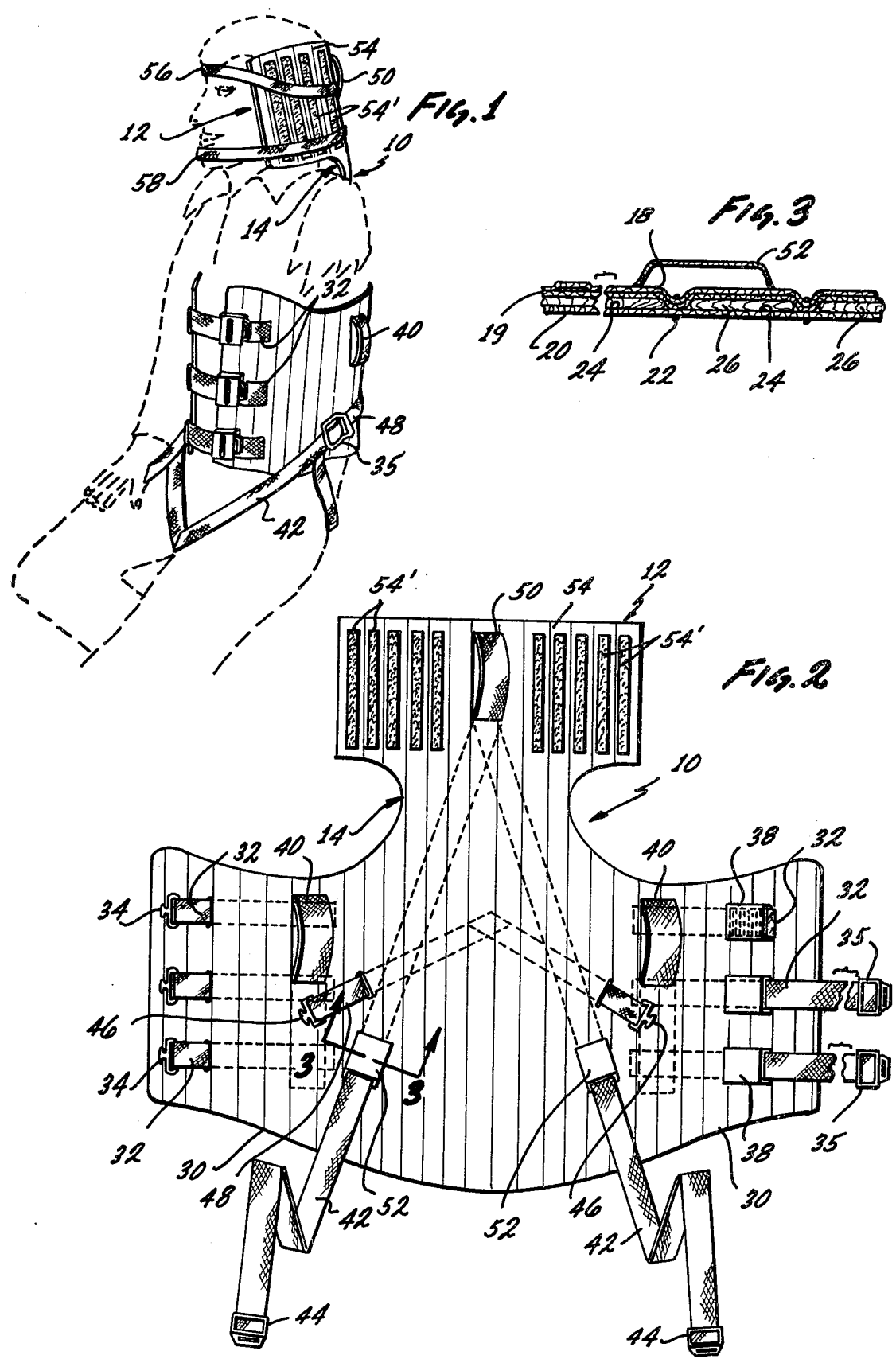

SPINAL RESTRAINT DEVICE

BACKGROUND OF THE INVENTION

The present invention relates to a spinal restraint device and is particularly concerned with such a device especially constructed and arranged for use with emergency patients. Such an occasion might arise in the case of an automobile accident, an injury to a player in an athletic event, a construction site accident, or any other type of an accident in which the injured person may have received a serious injury to his back or neck area.

The handling of an injured person requires special care in removing and carrying the injured person to a location equipped to administer medical treatment, such as hospitals or emergency centers.

Moving the injured person requires more than ordinary care in as much as a person is frequently injured in such a way that movement of the body causes further injury. Often the victim is trapped in a wreck in a position so that it is difficult to gain access to him. Haste in removing and transporting the person to adequate medical center facilities also tends to result in injury beyond that suffered in the actual accident. Thus, if the patient has had an injury to the spine, it is of the utmost importance to immobilize the body during the handling of the patient.

This need is recognized, and to some extent all litters and stretchers take account of the necessity for maintaining the patient in an immobile as well as comfortable a position as possible. Some devices have even been designed for the specific purpose of avoiding further bone or spine injury. However, the devices known to the art are far from satisfactory in a number of respects. Some are so complicated as to demand more time in use than is practical to employ. Other devices are unduly bulky. In addition, little attention has been given to the need for accommodating an injured person seated in the bucket seat of an automobile. The rigid back brace board utilized in most spinal restraint devices is next to impossible to slide down behind the back of an injured person sitting in a bucket seat. Spinal restraint devices utilizing this rigid back board construction are illustrated in U.S. Pat. Nos. 3,469,268 and 4,034,748.

In most of the present day spinal restraint devices, little or no provision has been made for hoisting the patient up out of a fairly inaccessible location while strapped in the spinal restraint device. Many of these present day spinal restraint devices do not have leg loop straps which results in the patient tending to slip downwardly in the device if it is lifted in some manner by gripping the top of the device. In those few spinal restraint devices that do have leg loops, the body of the patient still has a tendency to sag downwardly when the device is hoisted vertically.

It is an object of the invention to provide a novel spinal restraint device that can easily be slipped beneath the back of an injured victim in an automobile accident that is sitting in a bucket seat.

It is also an object of the invention to provide a novel spinal restraint device that wraps around the torso and head of an injured person thereby giving maximum immobilization of the injured person's head, neck, and back area.

It is another object of the invention to provide a novel spinal restraint device that is very compact in size when not being utilized and which easily and quickly unfolds when the necessity to use it occurs.

It is another object of the invention to provide a novel spinal restraint device which incorporates structure along its back surface for hoisting the injured person vertically out of inaccessible locations.

It is an additional object of the invention to provide a novel spinal restraint device that is economical to manufacture and relatively maintenance free.

It is a further object of the invention to provide a novel spinal restraint device that will provide maximum immobilization of the head, neck, and back of the injured person during his transportation to a medical treatment center.

SUMMARY OF THE INVENTION

The spinal restraint device has a body member having a head support portion, a neck support portion, and a back support portion. The body member has a front sheet-like layer of flexible material, a middle sheet-like layer of flexible material, and a rear sheet-like layer of flexible material. A couple of examples of material from which the front and rear sheets might be made are plastic, or a woven fabric. Laterally spaced longitudinal rows of stitching secures the front, middle, and rear sheet-like layers of flexible material together. These rows of stitching thereby form a plurality of longitudinal sleeves between the front sheet-like layer of flexible material and the middle sheet-like layer of flexible material. The use of stitching to form the sleeves is merely an example of one way to form the sleeves and the same result could also be obtained by a heat seam or an adhesive. The longitudinal sleeves extend substantially across the entire width of the body member. Stiffener members are located within each of the longitudinal sleeves to provide the spinal restraint device with longitudinal rigidity.

The back support portion has a body wrap-around arm portion extending laterally from each of its sides. The wrap-around arm portions extend laterally from the back support portion at a position downwardly from the top of the spinal restraint device such that the wrap-around arm portion passes under the patient's body below the patient's arm. A plurality of body cinching straps are attached to the wrap-around arm portions for securing the spinal restraint device across the patient's chest. Conventional type interlocking buckles having a male member and a female member are attached to the respective body cinching straps attached to the opposite wrap-around arm portions. The body cinching straps would have your conventional structure for lengthening or shortening the straps depending upon the girth of the injured person. Packing loops may also be formed on the rear surface of the wrap-around arm portions for storing the body cinching straps when the spinal restraint device is not being utilized. A hand grip lifting loop is also secured to the rear surface of each of the wrap-around arm portions to aid in transporting the injured person when a stretcher is not utilized.

The rear surface of the back support portion has a pair of leg loop straps fixed thereto. The free ends of each of the leg loop straps have a conventional buckle member thereon which attaches to a mating buckle member secured on the free ends of attaching straps which are also secured to the back support portions. The pair of leg loops straps may be formed from one continuous length of strap material with its intermediate portion passing upwardly along the interior of the body member until it reaches the head support position where a hoisting loop portion extends outwardly and rearwardly therefrom. This structure relieves much of the stress from the structure of the body member when the injured person is lifted vertically by some type of attachment to the hoisting loop. The stress produced by the lifting action travels down the length of the leg loop straps which in turn loop upwardly through the crotch area of the injured person where they are secured to the attaching straps. A pair of packing loops may also be formed on the rear surface of the back support portion for storage of the leg loop straps when the spinal restraint device is not being used. The attaching straps secured to the rear surface of the back support portion may also be formed from one continuous length of strap material.

The head support portion also has a head wrap-around arm portion extending laterally from each of its sides. Along the rear surface of the head support portion are a plurality of laterally spaced longitudinally extending Velcro hook and loop strips. These head wrap-around arm portions are secured in position around the injured person's head by a separate Velcro hook and loop strip that can be wound across the injured person's forehead or his chin and then secured to the longitudinally extending Velcro hook and loop strips.

When the novel spinal restraint device is not being utilized the wrap-around arm portions can be rolled inwardly from their free ends and the whole device can be stored in an elongated cylindrical configuration that can be slipped into an elongated carrying bag.

DESCRIPTION OF THE DRAWINGS

FIG. 1 is a side elevation view illustrating the novel spinal restraint device as it would be worn on an injured person;

FIG. 2 is a plan view of the rear surface of the novel spinal restraint device when it has been laid out on a flat surface; and FIG. 3 is a cross section view taken along lines 3—3 of FIG. 2.

DESCRIPTION OF THE PREFERRED EMBODIMENT

The novel spinal restraint device will be described by referring to FIGS. 1-3. The spinal restraint device is basically a body member generally designated numeral 10. The body member 10 has a head support portion 12, a neck support portion 14, and a back support portion 16.

The body member 12 has a front sheet-like layer 18 of flexible material, a middle sheet-like layer 19 of flexible material, and a rear sheet-like layer 20 of flexible material (see FIG. 3). Laterally spaced longitudinal rows of stitching 22 secure the front, middle, and rear sheet-like layers of flexible material together. These longitudinal rows of stitching 22 extend substantially across the entire width of the body member 10 and form a plurality of longitudinal sleeves 24. Stiffener members 26 are located within longitudinal sleeves 24.

Back support portion 16 has a body wrap-around arm portion 30 extending laterally from each of its sides. Each of these body wrap-around arm portions 30 have a plurality of body cinching straps 32 secured to them so that they will extend across an injured person's chest area. The body cinching straps 32 have conventional male and female buckle members 34 and 35 attached thereto. The rear surface of the one body wrap-around arm portion may also have a plurality of packing loops 38 into which the body cinching straps from that side may be stored when the spinal restraint device is not in use. Also attached to the rear surface of the wrap-around arm portions 30 are hand grip lifting loops 40.

A pair of leg loop straps 42 is attached to the rear surface of back support portion 16. The free ends of leg loop straps 42 have either a male or female member of a buckle 44 attached thereto. These buckle members 44 connect with interlocking buckle members 46 that are secured to the free ends of attaching straps 48 that are in turn attached to the rear surface of back support portions 16. As illustrated in FIG. 2, the attaching straps 48 may be formed from one continuous length of strap material. Likewise the leg loop straps 42 may also be formed from one continuous length of strap material with an intermediate portion of this length extending outwardly from the rear surface of head support portion 12 to form a hoisting loop 50. A pair of packing loops 52 are secured to the rear surface of back support portion 16 for storing the leg loop straps 42 when the spinal restraint device is not being used.

The head support portion 12 has a pair of wrap-around arm portions 54 extending laterally from each of its sides. The rear surface of the head support portion 12 also has a plurality of laterally spaced longitudinally extending Velcro hook and loop strips 54' secured thereto. As illustrated in FIG. 1, a forehead strap 56 and a chin strap 58, both of which have Velcro hook and loop structure on their inner surface, are secured around the injured person's head so that he can be secured to the longitudinally extending Velcro hook and loop strips 56.

What is claimed is:

1. A spinal restraint device comprising:
    a body member having a front sheet-like layer of flexible material and a rear sheet-like layer of flexible material.
    means forming a plurality of longitudinal sleeves between said front sheet-like layer of flexible material and said rear sheet-like layer of flexible material, stiffener members located within said longitudinal sleeves,
    said body member having a head support portion, a neck support portion and a back support portion, said head support portion being located adjacent the top of said neck support portion and said back support portion being located adjacent the bottom of said neck support portion, the longitudinal dimension of said head support portion being greater than the longitudinal dimension of said neck portion but less than the longitudinal dimension of said back support portion.
    the lateral dimension of said head support portion being greater than the lateral dimension of said neck support portion but less than the lateral dimension of said back support portion,
    said back support portion having wrap-around arm portions that extend laterally a predetermined dimension such that they pass substantially around the patient's torso and their longitudinal dimension is such that they extend substantially between the waist and the chest to provide rib area support, and
    a plurality of leg loop straps, each having one of their ends fixedly secured to the rear face of said back support portion, leg loop strap attaching means fixedly secured to the rear face of said back support portion for detachably receiving the free ends of said leg loop straps.

2. A spinal restraint device as recited in claim 1 wherein said longitudinal sleeves extend substantially across the entire width of said body member.

3. A spinal restraint device as recited in claim 1 wherein said means forming a plurality of longitudinal sleeves comprises laterally spaced longitudinal rows of stitching that secures said front and rear sheet-like layers of flexible material together.

4. A spinal restraint device as recited in claim 1 further comprising a hoisting loop attached to the rear surface of said head support portion.

5. A spinal restraint device as recited in claim 4 wherein said plurality of leg loop straps and said hoisting loop are formed from one continuous length of strap material.

6. A spinal restraint device as recited in claim 1 further comprising a plurality of packing loops on the rear surface of said back support portion for storably receiving said leg loop straps when the spinal restraint device is not being used.

7. A spinal restraint device as recited in claim 1 further comprising body cinching strap means attached to said wrap-around arm portions for securing the spinal restraint device across the patient's chest.

8. A spinal restraint device as recited in claim 1 wherein said head support portion has a head wrap-around arm portion extending laterally from each of its sides.

* * * * *